(12) United States Patent
Ten Eyck et al.

(10) Patent No.: US 7,787,726 B2
(45) Date of Patent: Aug. 31, 2010

(54) TEMPERATURE SENSING FABRIC

(75) Inventors: Lawrence G. Ten Eyck, Ellicott City, MD (US); Lynn E. Lynam, Bel Air, MD (US); Hua Xia, Altamont, NY (US); Kung-Li J. Deng, Waterford, NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 11/717,951

(22) Filed: Mar. 14, 2007

(65) Prior Publication Data

US 2008/0227349 A1 Sep. 18, 2008

(51) Int. Cl.
G02B 6/34 (2006.01)

(52) U.S. Cl. .............. 385/37; 442/60; 5/482; 374/130; 2/69

(58) Field of Classification Search ............. 385/12; 374/130; 442/60; 2/69; 5/482
See application file for complete search history.

(56) References Cited

U.S. PATENT DOCUMENTS

| | | | | |
|---|---|---|---|---|
| 4,907,132 A * | 3/1990 | Parker | | 362/556 |
| 5,562,027 A * | 10/1996 | Moore | | 100/35 |
| 6,080,690 A * | 6/2000 | Lebby et al. | | 442/209 |
| 6,381,482 B1 * | 4/2002 | Jayaraman et al. | | 600/388 |
| 6,727,197 B1 * | 4/2004 | Wilson et al. | | 442/301 |
| 6,981,935 B2 * | 1/2006 | Gustafson | | 492/10 |
| 7,154,081 B1 * | 12/2006 | Friedersdorf et al. | | 250/227.14 |
| 7,162,111 B2 * | 1/2007 | Baur et al. | | 385/13 |
| 7,189,944 B2 * | 3/2007 | Child et al. | | 219/212 |
| 7,336,862 B1 * | 2/2008 | Xai et al. | | 385/12 |
| 7,394,060 B2 * | 7/2008 | Beinhocker | | 250/227.14 |
| 7,581,456 B2 * | 9/2009 | Moore et al. | | 73/862.55 |
| 2004/0234218 A1 * | 11/2004 | Tao et al. | | 385/126 |
| 2004/0247228 A1 * | 12/2004 | Murad et al. | | 385/12 |
| 2007/0284112 A1 * | 12/2007 | Magne et al. | | 166/336 |
| 2008/0192778 A1 * | 8/2008 | Ohsono et al. | | 372/6 |
| 2008/0227349 A1 * | 9/2008 | Eyck et al. | | 442/60 |

* cited by examiner

Primary Examiner—Ellen Kim
(74) Attorney, Agent, or Firm—Roger M. Rathbun

(57) ABSTRACT

A blanket or article of wearing apparel for a subject such as an infant. A fiber optic temperature sensing element is integrated into the fabric by a process such as weaving. The temperature sensing element is a optic fiber having inscribed therein one or more fiber Bragg grating sensors such that a light is introduced into the optic fiber and that light directed onto the subject at a grating interface. A return light signal is received, either by a reflectance mode or a transmission mode, where the return light signal has a wavelength shift indicative of the temperature of the subject by Bragg resonant effect. Higher temperature sensitivity is obtained with a metal material of a high thermal expansion coefficient that is coated around the fiber sensor cladding.

17 Claims, 2 Drawing Sheets

TEMPERATURE SENSING FABRIC

FIELD OF THE INVENTION

The present invention relates to a fabric article for contacting a subject and, more particularly, to a fabric article that has included therein a sensing means for measuring the temperature of a subject.

BACKGROUND OF THE INVENTION

There are, of course, many instances where it is desirable to continuously sense the temperature of a subject. One example is in the care of newborns where the infant requires a stable temperature for survival and, therefore, it is necessary to keep a continual monitor of the temperature of the infant. As such, clinicians are required to frequently measure the temperature of the infant, ether independently or as a part of a thermal regulation device to ensure that a consistent body temperature is maintained.

At the present, however, the temperature readings are only periodically taken, as no continuous recording device exists for measuring the temperature of the infant during a thermal challenge. As a result, discharge of the infant from the hospital is often delayed for days while the infant establishes auto-regulation of its temperature.

One means of continually monitoring the temperature of an infant is to affix one or more temperature sensors, such as thermistors, to the skin of the infant and then continually measure the temperature signals from the sensors. There is, however a difficulty with such use of temperature sensors affixed to the infant's skin since the sensors can cause sores on the infant and there is always a problem with the troublesome wires that connect the sensor to the monitoring device which can become disconnected or simply create an impediment to the access to the infant by attending personnel. In addition, with the use of electrically activated sensors, there is a problem with interference by other equipment in the vicinity of the temperature sensors and which can cause inaccuracy or total loss of signal from the temperature sensors.

There have been certain coverings that have been published that have some means of measuring the temperature and, as an example, in U.S. Pat. No. 4,672,176 of Kishimoto et al, there a blanket that includes a plurality of temperature sensors affixed to the covering, however, those sensors are electrically activated and are subject to electrical interference from other equipment used in the care of an infant or other patient.

There is a technology that is present available but not yet applied or used in a temperature sensing fabric and that technology involves the use of a Fiber Bragg-Grating (FGB) temperature sensor and which is inscribed into an optical fiber by standard ultraviolet laser light fabrication process. Such FBG sensors have been used in medical applications, for example, to obtain a temperature profile of a patient. See In-Fiber Bragg-Grating Temperature Sensor System For Medical Applications, Journal of Lightwave Technology, Vol. 15, No. 5 May, 1997, pages 779-785. As noted in that article, one of the advantages of the FBG sensor for temperature sensing is that there is no problem with radio-frequency interference. Another advantageous property of the FBG sensor is that it can be inscribed at any location along an optical fiber and the FBG sensors can also be cascaded in the optical fiber without increasing the diameter of that optical fiber. The spatial resolution can be less than a few millimeters and the maximum length of the FBG sensor distribution can be a few mils. The diameter and length of the fiber sensors are 0.25 mm. and 5.0 mm made from biocompatible silicon dioxide glass material.

It would, therefore, be desirable to have a fabric article, particularly an infant blanket, that would provide warmth and comfort for the infant having efficient, temperature sensors actually integrated into the woven blanket to sense individually located temperatures or the overall temperature of the subject by using the aforementioned technology. It would also be advantageous to have other fabric articles having temperature sensing capability integrated into the fabric article including, but not limited to, articles of clothing and the like.

BRIEF SUMMARY OF THE INVENTION

Accordingly, the present invention relates to a fabric article for contacting a subject, particularly an infant. As described herein as an exemplary embodiment, one use of the present fabric article is as a blanket for infants, however, as will be appreciated, the present woven fabric having temperature sensing capability can be used for many other uses where the temperature of a subject is desired to be monitored, including articles of clothing for a subject such as pajamas for an infant. With the exemplary embodiment and as will be described herein, the blanket is a woven blanket that can promote warmth and comfort to the infant in the manner of a normal infant blanket.

With the present blanket, however, there is integrated into that blanket, at least one fiber optic temperature sensing element that can sense the temperature of the infant when the blanket is placed over the infant.

By integrated, it is meant that the fiber optic temperature sensing element is actually incorporated into the optical fiber by being woven therein or otherwise actually intertwined with the woven blanket so that the blanket can be used in its normal manner of covering the infant and yet the temperature sensing capability is provided by the sensing element or elements being integrated into the blanket.

Thus the blanket itself is a woven fabric and, in an exemplary embodiment, the optical fiber or fibers is woven into the blanket. The weaving of optical fibers is known and, as an example, a "Smart Shirt" is shown in an article entitled "Fiber optics in textile", by Kami Emirhan, $3^{rd}$ International symposium of Interactive Design, 2005 which is described as a t-shirt woven with fiber optics. Optical fibers are also woven into a pad for transmitting light for phototherapy to an infant in alleviating bilirubinemia and a woven pad is shown and described in U.S. Pat. No. 4,907,132 of Parker.

The optical fibers that are integrated into the blanket of the present invention each has one or more fiber Bragg grating (FBG) sensors incorporated into the optical fiber or fibers. As such, there may be one or a plurality of such FBG sensors in each optical fiber in a predetermined pattern or any pattern that is customized to sense a particularly important or critical area of the infant. With such a customized array, however, it would necessitate the blanket being properly oriented with respect to the infant.

The present temperature sensing blanket is therefore a part of a temperature sensing system that includes a source of light that is introduced into the optical fibers to reach each of the FBG sensors within the fiber. That light, in accordance with the principles of the FBG's, passes out from the FBG sensor to reach the infant's skin and the return light has a wavelength shift that is indicative of the temperature of that skin. The return light signal is then passed back through the optical fiber to be received and interpreted by signal processing circuitry to determine the skin temperature of the infant. The temperature sensing is thereby dependent upon the periodicity of changes of the grating, and infant body temperature will induce metal film thermal expansion that modifies the periodicity of the fiber Bragg grating proportionally. To obtain a maximum temperature sensitivity the FBG sensor can include a metallic material coating the cladding surface and which may be applied by a magnetron sputtering method. The magnetic material can be, but is not limited to, Al, Au, Ni and a combination of non-corrosive alloys.

An exemplary embodiment of the present fiber cable is made of a metallized single-mode fiber material that has a 0.125 mm. diameter cladding and a 0.09 mm. diameter fiber core. The multiple fiber cables can be coupled into an interrogation system by an optical switcher or multi-branch optical couplers. The embodiment has introduced a tunable laser of 80 nm bandwidth for fiber FBG sensor interrogation and each sensor wavelength spacing is around 0.5 nm. Thus, 160 fiber sensors can be handled in one channel and 640 fiber FBG sensors in a system of 4 channels. The wavelength shift of each FBG sensor is calibrated by a NIST gas cell and the wavelength shift and reflectance or transmittance simultaneously monitored with software wireless and remotely.

In summary, therefore, the present blanket and system can sense the temperature of a subject by simply placing the blanket in thermal contact with the subject. The FBG sensors in the optical fibers integrated into the blanket can sense the temperature of the subject and thus can continuously monitor the temperature of the subject.

These and other features and advantages of the present invention will become more readily apparent during the following detailed description taken in conjunction with the drawings herein.

DETAILED DESCRIPTION OF THE INVENTION

Figure 1:
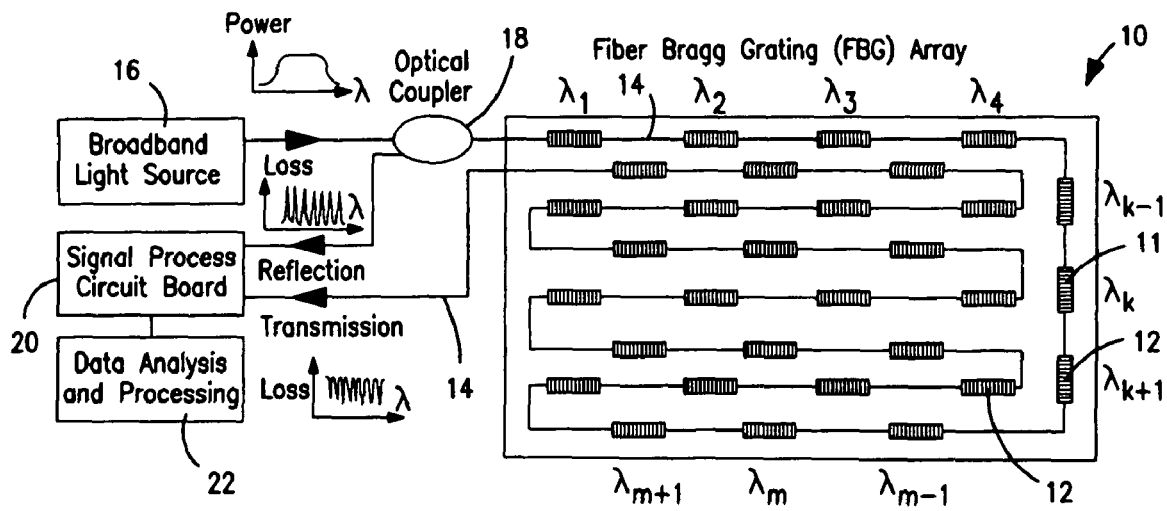
FIG. 1 is a schematic view of a temperature sensing blanket constructed in accordance with the present invention.

Referring now to FIG. 1, there is shown a schematic view of a temperature sensing blanket 10 of the present invention. As can be seen the blanket 10 has a plurality of fiber Bragg gratings (FBG) sensors 12 inscribed therein into an optical fiber 14. The FBG sensors 12 are shown to all be connected in series and are therefore all interconnected by the optical fiber 14, however, the blanket 10 may provide isolated groups of series connected FBG sensors so that the blanket 10 can sense the temperature independently at different selected locations of the subject.

There is a broadband light source 16 that provides the light for the optical fiber 14 so as to reach each of the FBG sensors 12. That light source 16 may be a tungsten lamp or other source of the broad band light.

As shown, the light from the broadband light source 16 passes through an optical coupler 18 and thus into the FBG sensors 12 within the optical fiber 14 that is integrated into the temperature sensing blanket 10. A reflective light signal from the FBG sensors 12 returns along the optic fiber 14 in a rearward direction and passes through the optical coupler 18 to reach the signal processor 20.

There is also a transmitted light signal that passes through each of the FBGs 12 in series and reaches the signal processor 20.

As such, either the reflected light signal or the transmission light signal can be used in carrying out the present invention as both provide a light signal that determines a shift in wavelength between the emitted light and the return light and which is indicative of the sensed temperature.

The light signals from the reflective mode or the transmission mode are processed by the signal processor 20 and the data is entered into the data analysis and processing block 22 where the determination of the temperature of the subject sensed by the FBG sensors 12 is processed and derived.

Figure 2:
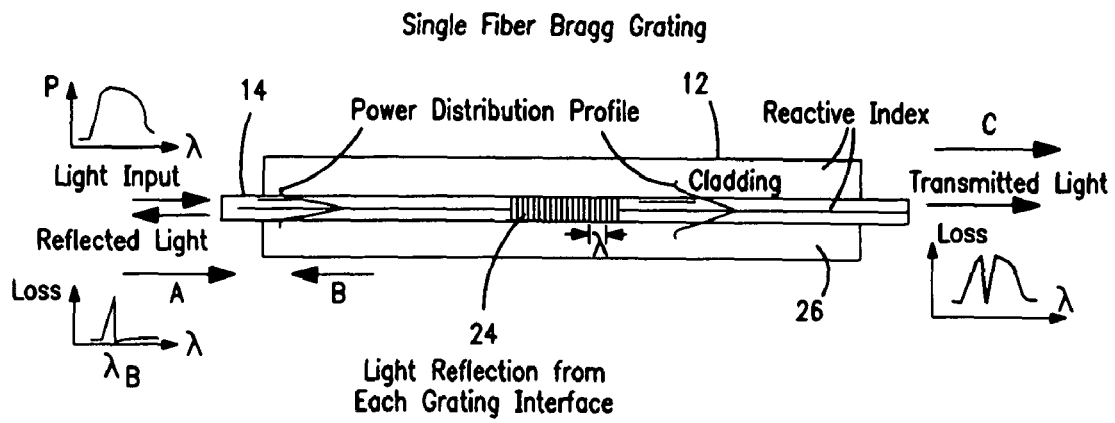
FIG. 2 is a side, schematic view of a single fiber Bragg grating sensor used with the present invention.

Turning now to FIG. 2, there is a side schematic view of a single fiber Bragg grating sensor 12 used with the present invention. The broad band light enters the optic fiber 14 in the direction of the arrow A and proceeds along the optic fiber 14 to a grating interface 24 where the light passes out of the optic fiber 14 to the surrounding area through a cladding 26. When the temperature sensing blanket 10 is in a heat conductive relationship to a subject, such as to an infant, the light from the grating interface 14 contacts the infant and creates a return light signal having a wavelength shift that is indicative of the skin temperature of that infant.

Accordingly, the return signal that now contains information as to the temperature of the infant, is either reflected back along the optic fiber 14 and is emitted in the direction of the arrow B as in a reflective mode or continues along the optic fiber 14 to be emitted in the direction of the arrow C as in a transmission mode.

Figure 3:
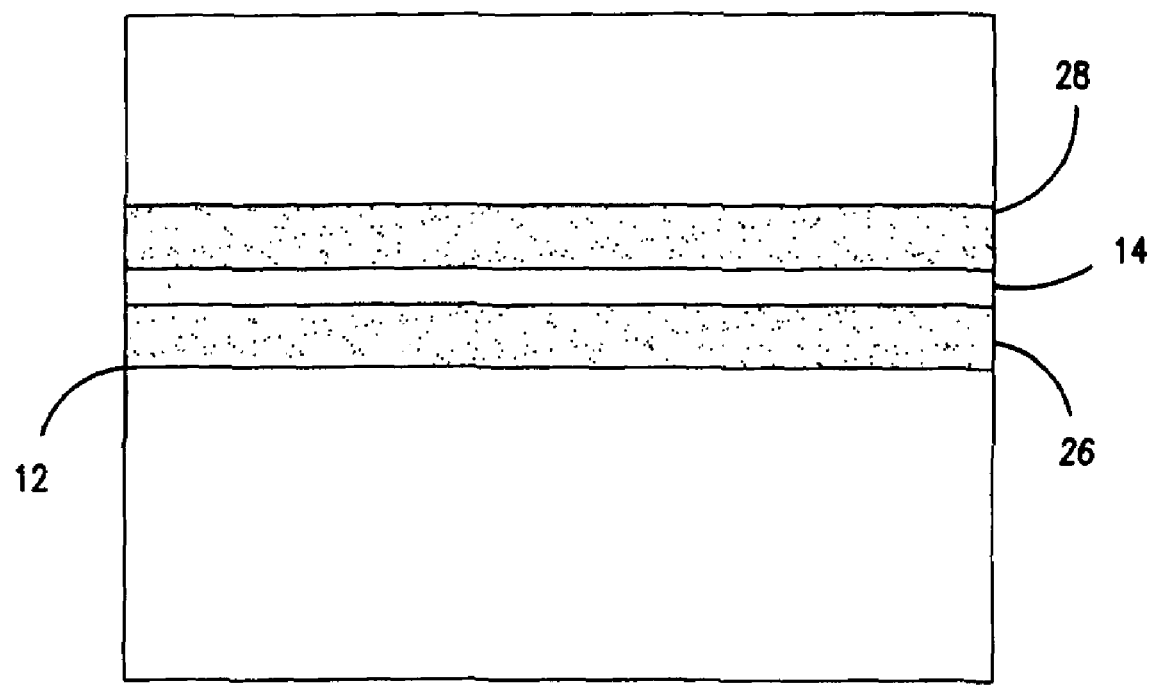
FIG. 3 is a cross-sectional view of a metal fiber Bragg grating sensor that can be used with the present invention.

Turning now to FIG. 3, there is shown a metal coated FBG sensor 12 having a metal coating 28 and which can be a 20 nm gold alloy which provides high-sensitivity temperature sensing. The metal coating 28 on the surface of the FBG sensor 12 will enhance the temperature sensitivity more than 20 times due to the much larger thermal expansion coefficient of metal than silica glass fiber material. The use of the metal coating 28 on the surface of the FBG sensor 12 is of good thermal conductivity so that the FBG sensor 12 can provide a fast response to infant temperature variation.

Those skilled in the art will readily recognize numerous adaptations and modifications which can be made to the temperature sensing blanket and use thereof which will result in an improved temperature sensing blanket, yet all of which will fall within the scope and spirit of the present invention as defined in the following claims. Accordingly, the invention is to be limited only by the following claims and their equivalents.

We claim:

1. A temperature sensing fabric article adapted to contact at least a portion of a subject, said fabric article comprising a material comprised of woven optical fibers with at least one of the optical fibers having a plurality of fiber Bragg grating optic sensors integrated thereinto to sense the temperature of the subject at a plurality of locations by creating a detectable shift in the wavelength of light radiation emitted from and returning to the fiber Bragg grating optic sensors.

2. The temperature sensing fabric article of claim 1 wherein the article is an article of clothing.

3. The temperature sensing fabric article of claim 1 wherein the article is a blanket.

4. The temperature sensing blanket of claim 3 wherein the subject is an infant and the blanket senses the skin temperature of an infant.

5. The temperature sensing fabric article of claim 1 wherein the fiber Bragg grating sensor is coated with a high heat conductivity material.

6. The temperature sensing fabric article of claim 5 wherein the fiber Bragg grating sensor is coated with a material containing Al, Au or Ni.

7. A system for measuring the temperature of a subject comprising an article comprising a woven material of optical fibers having a plurality of fiber Bragg grating optic temperature sensors integrated into at least one of the optical fibers, a light source for transmitting light to the fiber Bragg grating optic temperature sensors, the fiber Bragg grating optic temperature sensors directing that light onto the subject and receiving light reflected from the subject having a wavelength shift of the light indicative of the temperature of a subject, a light sensor for receiving light received by the fiber optic temperature sensors and a signal processor adapted to interpret the wavelength shift of the light directed and received by the fiber Bragg grating optic temperature sensors to determine the temperature of a subject at multiple locations.

8. The system as defined in claim 7 wherein the article comprises a blanket.

9. The system as defined in claim 7 wherein the article comprises an article of clothing.

10. The system as defined in claim 7 wherein the system measures the skin temperature of an infant.

11. The system as defined in claim 7 wherein the light is transmitted to and received from the at least one fiber optic temperature sensor by an optical fiber.

12. The system as defined in claim 1 wherein the fiber Bragg grating sensor is coated with a high heat conductivity material.

13. The system as defined in claim 12 wherein the fiber Bragg grating sensor is coated with a material containing Al, Au or Ni.

14. The system as defined in claim 7 wherein the at least one fiber Bragg grating optic temperature sensor comprises a plurality of fiber Bragg grating optic sensors.

15. A method of sensing the temperature of a living subject comprising:
   providing an article comprising a material of woven optical fibers having at least one fiber Bragg grating optic temperature sensor integrated into one of the optical fibers,
   placing the article in thermal communication with the living subject,
   providing a light signal to the at least one fiber Bragg grating optic temperature sensor whereby the at least one fiber Bragg grating optic temperature sensor directs the light signal onto the subject and receives a return light signal from the living subject having a wavelength shift indicative of the temperature of the living subject,
   determining the temperature of the subject by interpreting the wavelength shift indicative of the temperature of the living subject in the return light signal.

16. The method of claim 15 wherein the step of providing an article comprises providing an article of clothing having at least one fiber Bragg grating optic temperature sensor inscribed within an optical fiber.

17. The method of claim 15 wherein the step of providing an article comprises providing a blanket having at least one fiber Bragg grating optic temperature sensor inscribed within an optical fiber.

* * * * *